(12) United States Patent
Mano et al.

(10) Patent No.: US 7,638,516 B2
(45) Date of Patent: Dec. 29, 2009

(54) AGENT FOR THERAPEUTIC TREATMENT OF OPTIC NERVE DISEASES AND THE LIKE

(75) Inventors: Tomiya Mano, Osaka (JP); Shunji Sogou, Osaka (JP); Eri Inoue, Hyogo (JP)

(73) Assignee: Mei Co., Ltd., Hyogo (JP)

( * ) Notice: Subject to any disclaimer, the term of this patent is extended or adjusted under 35 U.S.C. 154(b) by 201 days.

(21) Appl. No.: 11/477,854

(22) Filed: Jun. 30, 2006

(65) Prior Publication Data

US 2006/0247293 A1   Nov. 2, 2006

Related U.S. Application Data

(63) Continuation of application No. 10/312,502, filed as application No. PCT/JP01/05585 on Jun. 28, 2001, now abandoned.

(30) Foreign Application Priority Data

Jun. 29, 2000   (JP) ............................. 2000-197250

(51) Int. Cl.
    *A01N 43/58* (2006.01)
(52) U.S. Cl. .................................... 514/247
(58) Field of Classification Search ........................ None
    See application file for complete search history.

(56) References Cited

U.S. PATENT DOCUMENTS

| 4,857,542 A | 8/1989 | Nishi et al. |
| 5,837,723 A | 11/1998 | Watanabe |

FOREIGN PATENT DOCUMENTS

| DE | 35 33 662 | 3/1986 |
| EP | 609822 | 8/1994 |
| EP | 633025 | 1/1995 |
| FR | 2608045 | 6/1988 |
| JP | 03 215425 | 9/1991 |
| JP | 9-278652 | 10/1997 |
| JP | 10 218771 | 8/1998 |
| WO | 93/00088 | 1/1993 |
| WO | 98/32863 | 7/1998 |

OTHER PUBLICATIONS

Opere et al., Regulation of Uveal Sympathetic Neurotransmission by Peroxides. Investigative Ophthalmology & visual Science, Apr. 1997.*
Abstract of: Cheung et al., Z. H. "Mixture of American ginseng extract, Ginkgo biloba extract and St. John's wort extract enhances the survival of axotomized retinal ganglion cells." 30th Annual Meeting of the Society of Neuroscience; New Orleans, LA, USA; Nov. 4-9, 2000. PUB Society for Neuroscience Abstracts, vol. 26, nr. 1-2, abstract nr. 123.16.
Babovic et al., S. "Role of reactive oxygen species in optic nerve compression injury: A preliminary study." Annals of Plastic Surgery. United States. ISSN 0148-7043. vol. 40, nr. 2, pp. 156-159 (1998).
Bemired et al., S. "Effect of radical scavengers on ocular hemodynamics and on the visual field in primary open angle glaucoma." Annual Meeting of the Association for Research in Vision and Ophthalmology; Fort Lauderdale, Florida, USA; Apr. 21-26, 1996. Investigative Ophthalmology and Visual Science, vol. 37, nr. 3, p. S270, CONF. (1996).
Eschweiler et al., G. W. "Free-radical scavengers support retinal ganglion cell survival after traumatic optic nerve lesions." 26th Annual Meeting of the Society for Neuroscience; Washington, D.C., USA; Nov. 16-21, 1996. Society for Neuroscience Abstracts, vol. 22, nr. 1-3, p. 317, CONF. (1996).
Roth et al., Current Eye Research, vol. 16, pp. 875-885, 1997.

* cited by examiner

*Primary Examiner*—Eric E. Silverman
(74) *Attorney, Agent, or Firm*—Wenderoth, Lind & Ponack, LLP

(57) ABSTRACT

The medicament for therapeutic and/or prophylactic treatment of the present invention has a suppressing action on the retinal degeneration induced by transient retinal ischemia, which is verified by the results for suppressing effect on retinal degeneration in transient retinal ischemia eye. Therefore, the medicament of the present invention has a therapeutic and/or prophylactic effectiveness on diseases in optic nerve and the like.

2 Claims, 1 Drawing Sheet

AGENT FOR THERAPEUTIC TREATMENT OF OPTIC NERVE DISEASES AND THE LIKE

Figure 1:
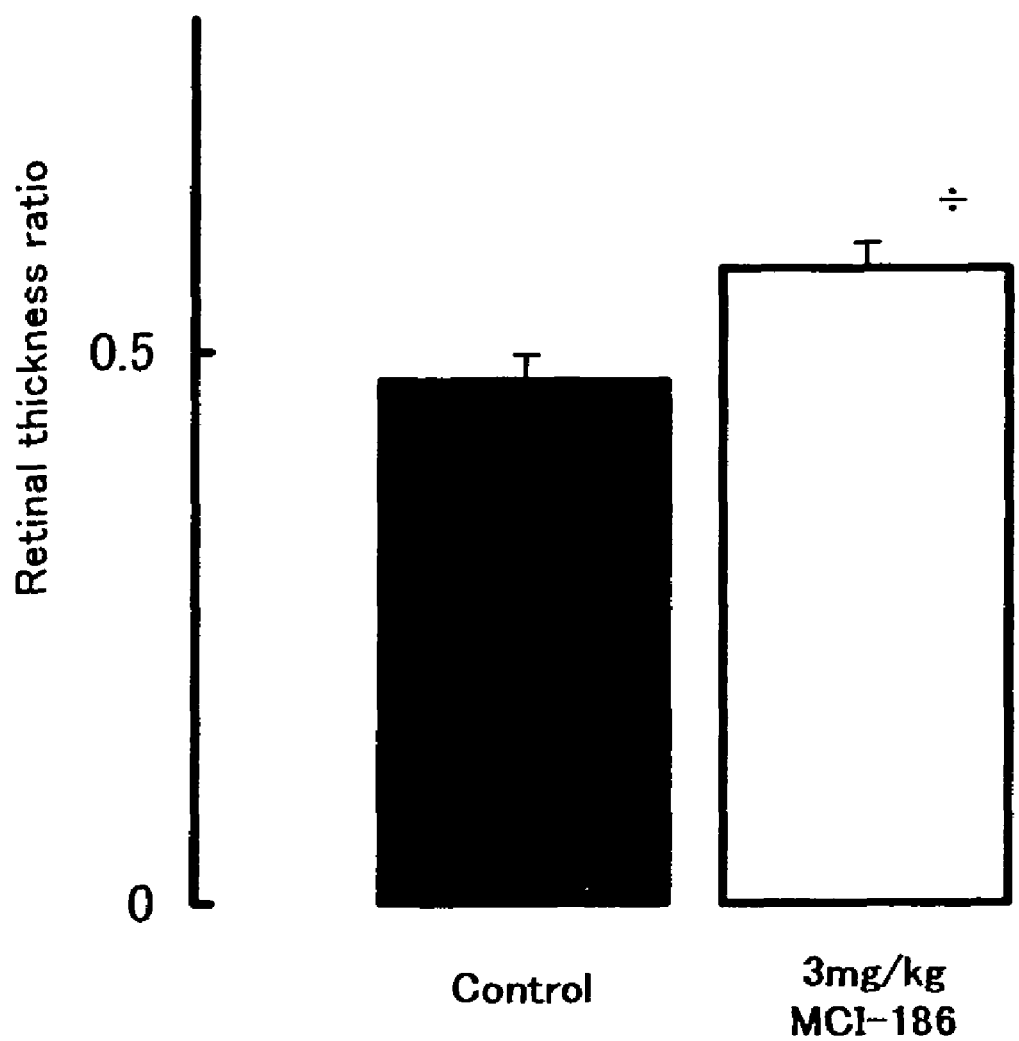

This application is a continuation application of Ser. No. 10/312,502 filed Dec. 27, 2002 now abandoned, which is a U.S. national stage of International Application No. PCT/JP01/05585 filed Jun. 28, 2001.

TECHNICAL FIELD

The present invention relates to a medicament which comprises 3-methyl-1-phenyl-2-pyrazolin-5-one or a pharmaceutically acceptable salt thereof as an active ingredient and which is used for therapeutic treatment and/or prophylactic treatment of diseases in optic nerve as well as a) retinal circulatory disorders caused by retinal vein occlusion and the like, b) retinal circulatory disorders caused by retinal artery occlusion and the like, c) retinal disorders caused by surgery, trauma and the like, d) retinal disorders caused by virus, bacteria, fungi and the like, e) macular diseases such as age-related macular degeneration, f) retinal degenerative diseases such as retinitis pigmentosa, g) retinal detachment and h) retinal disorders caused by drugs toxic to the retina such as phenothiazine.

BACKGROUND ART

As for neural cell death and neuroprotection in the ophthalmological field, recent studies have revealed that neural cell death occurs in many diseases in optic nerve. Although a mechanism for inducing the neural cell death in diseases of optic nerve has not yet been fully elucidated, retinal ischemia is considered to be one of factors. Ischemia is defined as a lack or an insufficiency of blood circulation in tissues, and anoxemia caused by reduction of ocular blood flow due to increased intraocular pressure (IOP) is considered to play an important role in degeneration of optic nerve. On the basis of these findings, the IOP is lowered by drug therapy or surgery in current glaucoma treatment. Although its effectiveness has been proved by many studies, there are many clinical cases where IOP cannot be lowered sufficiently or those where lowering of IOP is ineffective. From a long-term viewpoint, there is a risk that patients may go blind at a considerable rate despite the therapeutic treatment. Under the circumstances, for therapeutic treatment of glaucoma, establishment of a therapeutic strategy is also desired in which direct neuroprotection for an optic nerve is seriously considered from a viewpoint of improvement of blood flow and suppression of cell death, as well as effect of lowering IOP (Exp. Eye Res. 69, 331-342 (1999) and the like).

It has been reported that a compound having hydroxy radical-scavenging action such as 3-methyl-1-phenyl-2-pyrazolin-5-one can prevent onset or progression of ocular diseases such as cataract and retinopathy (Japanese Patent Unexamined Publication (Kokai) No. Hei 7-25765). However, no report has been made on inhibitory action on neural cell death in the optic nerve.

In addition to diseases in optic nerve, each of a) retinal circulatory disorders caused by retinal vein occlusion and the like, b) retinal circulatory disorders caused by retinal artery occlusion and the like, c) retinal disorders caused by surgery, trauma and the like, d) retinal disorders caused by virus, bacteria, fungi and the like, e) macular diseases such as age-related macular degeneration, f) retinal degenerative diseases such as retinitis pigmentosa, g) retinal detachment, and h) retinal disorders caused by drugs toxic to the retina such as phenothiazine (hereinafter, these diseases will be referred to as "diseases in optic nerve and the like") develops severe ocular function disorders, for which no appropriate therapeutic treatment is available. Therefore, an effective therapeutic medicament for these diseases is strongly desired. Accordingly, an object of the present invention is to provide a novel medicament for therapeutic treatment and/or prophylactic treatment of diseases in optic nerve and the like.

DISCLOSURE OF THE INVENTION

The inventors of the present invention made a profound study of the mechanism of neural cell death in the optic nerve, and they considered that, if a therapeutic method can be developed which enables suppression of the cell death, the method will lead to improvement of curative rate of these intractable diseases. They thus conducted various researches to achieve the aforementioned object, and as a result, they found that compounds having hydroxy radical-scavenging action, in particular, 3-methyl-1-phenyl-2-pyrazolin-5-one (hereinafter, this compound will be sometimes abbreviated as "MCI-186") or a pharmaceutically acceptable salt thereof, had neuroprotective action in the optic nerve and were useful for therapeutic treatment of diseases in optic nerve and the like. The present invention was achieved on the basis of these findings.

The present invention thus provides a medicament for therapeutic and/or prophylactic treatment of an optic nerve disease and the like, which comprises 3-methyl-1-phenyl-2-pyrazolin-5-one or a pharmaceutically acceptable salt thereof as an active ingredient; and the aforementioned medicament for therapeutic and/or prophylactic treatment of the disease in optic nerve and the like, which is any one of an oral preparation, an injection, an eye drop, an ointment, or a sustained-release preparation to be left under the eyelid. More specifically, the present invention provides the aforementioned medicament for therapeutic treatment and/or prophylactic treatment, wherein the disease in optic nerve is any one of: a) inflammatory diseases such as optic neuritis, b) diseases caused by circulatory disorders such as ischemic optic neuropathy, c) optic nerve disorders caused by compression of the optic nerve due to surgery, trauma, tumor and the like, or due to edema and the like, d) optic nerve toxic diseases caused by ethambutol, alcohol and the like, e) optic nerve disorders caused by a refractive surgery and the like, and f) glaucoma.

BEST MODE FOR CARRYING OUT THE INVENTION

The present invention will be explained in detail below.

The disease in optic nerve includes: a) inflammatory diseases such as optic neuritis, b) diseases caused by circulatory disorders such as ischemic optic neuropathy, c) optic nerve disorders caused by compression of the optic nerve due to surgery, trauma, tumor and the like, or due to edema and the like, d) optic nerve toxic diseases caused by ethambutol, alcohol and the like, e) optic nerve disorders caused by a refractive surgery, f) glaucoma and the like.

The 3-methyl-1-phenyl-2-pyrazolin-5-one or a pharmaceutically acceptable salt thereof of the present application is widely applicable in the ophthalmological field, including the aforementioned diseases in optic nerve and the like, on the basis of the neuroprotective action in the optic nerve.

The active ingredient of the medicament of the present invention, of which typical example includes MCI-186 or a pharmaceutically acceptable salt thereof, is the compounds disclosed in Japanese Patent Publication (Kokoku) Nos. Hei 5-35128 and Hei 5-31523, and can be prepared by the methods described in these patent publications or similar methods thereto. Examples of the pharmaceutically acceptable salt include salts with a mineral acid such as hydrochloric acid, sulfuric acid, hydrobromic acid, phosphoric acid and the like; salts with an organic acid such as methanesulfonic acid, p-toluenesulfonic acid, benzenesulfonic acid, acetic acid, glycolic acid, glucuronic acid, maleic acid, fumaric acid, oxalic acid, ascorbic acid, citric acid, salicylic acid, nicotinic acid, tartaric acid and the like; salts with an alkali metal such as sodium, potassium and the like; salts with an alkali earth metal such as magnesium, calcium and the like; salts with ammonia or with an amine such as tris(hydroxymethyl)aminomethane, N,N-bis(hydroxyethyl)piperazine, 2-amino-2-methyl-1-propanol, ethanolamine, N-methylglucamine, L-glucamine and the like.

For clinical application of the active ingredient of the medicament of the present invention, for example, MCI-186 or a pharmaceutically acceptable salt thereof, MCI-186 or a pharmaceutically acceptable salt thereof, per se, is used or the substance is used as a pharmaceutical composition formulated with a pharmaceutically acceptable vehicle. When used as an eye drop, it is preferred that one to two drops of 1 to 20 mg/ml of the above-mentioned compound are applied to the eye once to several times a day; when used orally, it is preferred that 1 to 100 mg/kg of the above-mentioned compound is administered once to three times a day; and for an intravenous injection, it is preferred that 0.01 to 200 mg of the above-mentioned compound is administered twice to five times a day, or said dose is administered as a continuous drip infusion. For rectal administration, it is preferred that 1 to 100 mg/kg of the above-mentioned compound is administered once to three times a day. Further, the above-mentioned compound can be added in an intraocular perfusion fluid and then used. The above-mentioned doses may be changed depending on the age, type of pathema, sexuality, symptoms and the like of a patient.

Form of pharmaceutical composition, i.e., pharmaceutical formulations, include an aqueous eye drop, a non-aqueous eye drop, a suspended eye drop, an emulsified eye drop and the like as the eye drops. For preparation of the eye drops, an aqueous solvent such as sterilized and purified water, physiological saline solution and the like, or a non-aqueous solvent such as vegetable oils including cottonseed oil, soybean oil, sesame oil, peanut oil and the like is used, and the preparation is carried out by dissolving or suspending MCI-186 or a pharmaceutically acceptable salt thereof in the solvent. For the preparation, isotonizing agents, pH adjusting agents, thickeners, suspending agents, emulsifiers, preservatives and the like may be appropriately added, if necessary. Examples of the isotonizing agent include sodium chloride, boric acid, sodium nitrate, potassium nitrate, D-mannitol, glucose and the like; examples of the pH adjusting agent include boric acid, anhydrous sodium sulfite, hydrochloric acid, citric acid, sodium citrate, acetic acid, potassium acetate, sodium carbonate, borax and the like; examples of the thickener include methyl cellulose, hydroxypropylmethyl cellulose, polyvinyl alcohol, sodium chondroitin sulfate, polyvinylpyrrolidone and the like; examples of the suspending agent include polysorbate 80, polyoxyethylene hydrogenated castor oil 60, polyoxy castor oil and the like; examples of the emulsifier include egg yolk lecithin, polysorbate 80 and the like; and examples of the preservative include benzalkonium chloride, benzethonium chloride, chlorobutanol, phenylethyl alcohol, p-hydroxybenzoates and the like.

For pharmaceutical formulations other than eye drops, MCI-186 or a pharmaceutically acceptable salt thereof may be used in a composition containing ordinarily used pharmaceutical vehicles such as excipients or other additives. Such vehicles may be either solid or liquid. Examples of the solid vehicle include lactose, kaolin, sucrose, crystalline cellulose, corn starch, talc, agar, pectin, acacia, stearic acid, magnesium stearate, lecithin, sodium chloride and the like, and examples of the liquid vehicle include syrup, glycerol, peanut oil, polyvinylpyrrolidone, olive oil, ethanol, benzyl alcohol, propylene glycol, water and the like.

When a solid vehicle is used, the formulations may be in the form of tablets, powders, granules, hard gelatin capsules, suppositories, troches and the like. For such preparation, an amount of the solid vehicle may be freely chosen. Preferably, the amount is chosen so as to be from about 1 mg to about 1 g.

When a liquid vehicle is used, the formulations may be in the form of syrups, emulsions, soft gelatin capsules, or sterilized solutions for injection filled in an ampoule, or aqueous or non-aqueous suspensions.

For preparation of the formulations according to the present invention, it is also preferred to formulate MCI-186 or a pharmaceutically acceptable salt thereof as a sustained-release form, for example, by clathration in cyclodextrin or encapsulation in liposomes.

The medicament for ocular diseases in the present invention thus obtained is used as a medicament for prophylactic or therapeutic treatment of diseases in optic nerve and the like.

EXAMPLE

The present invention will be explained in more detail by referring to the following example. However, the present invention is not limited by the following example so far that it lies within the gist thereof.

Suppressing Effect on Retinal Degeneration in Transient Retinal Ischemia (Test Method)

Wister male rats (body weight of about 200 g) were used. Each animal was subjected to sufficient warming treatment by using a thermal plate under anesthesia, and the head was fixed by using a stereotaxic apparatus. In order to induce transient retinal ischemia, IOP was maintained at 130 mmHg for 50 minutes by injecting intraocular irrigating solution into the anterior chamber via the cornea using an infusion tube and 30 G injection needle which were connected to a bottle held at 174 cm above the eyes (ocular hypertension treatment) according to the method of Akaike (Folia Pharmacologica Japonica, 111, pp. 97-104 (1998)). The ocular hypertension treatment was performed only on the right eye, and the left eye was left untreated. Immediately before and after the ocular hypertension treatment, a physiological saline solution or a dose of 3 mg/kg of MCI-186 was injected to the caudal vein. The efficacy of the medicament in the present invention was evaluated by measuring the thickness of the retina including an inner plexiform layer, comprised of a synapse of ganglion cells, bipolar cells and amacrine cells where marked degeneration (thinning) had been shown to be caused by retinal ischemia. That is, a light-microscopic section of the retina was prepared 7 days after the ocular hypertension treatment, and the thickness of the retina was measured under microscope by using a micrometer (thickness from inner plexiform layer to inner nuclear layer).

(Test Results)

FIG. 1 shows the retinal thickness ratios calculated as [Retinal thickness in the ocular hypertension treated eye/Retinal thickness in the normal eye, retinal thickness: total thickness of from inner plexiform layer to inner nuclear layer] 7 days after the ocular hypertension treatment. Data represent means±SEM. As for the number of animals, the control group consisted of 10 rats, and the MCI-186 group consisted of 11 rats. Symbol * represents a significant difference relative to the control group (p<0.01).

As shown in FIG. 1, MCI-186 significantly suppressed the retinal degeneration induced by transient retinal ischemia.

INDUSTRIAL APPLICABILITY

From the results of the inhibitory effect on retinal degeneration in transient retinal ischemia, it is concluded that the medicament for therapeutic and/or prophylactic treatment of the present invention for diseases in optic nerve and the like has a suppressing action on retinal degeneration induced by transient retinal ischemia. Therefore, the medicament of the present invention has a therapeutic and/or prophylactic effectiveness on diseases in optic nerve and the like.

The present application was filed with claiming the conventional priority based on Japanese Patent Application No. 2000-197250.

What is claimed is:

1. A method for suppressing death of optic nerve cells during ocular hypertension in a patient with glaucoma, which comprises administering an effective amount of 3-methyl-1-phenyl-2-pyrazolin-5-one or a pharmaceutically acceptable salt thereof to the patient.

2. The method according to claim 1, wherein the 3-methyl-1-phenyl-2-pyrazolin-5-one or a pharmaceutically acceptable salt thereof is administered in an oral formulation, an injection, an eye drop, an ointment, or a sustained-release preparation to be left under the eyelid.

* * * * *